United States Patent
Kirk

(10) Patent No.: US 6,455,322 B1
(45) Date of Patent: Sep. 24, 2002

(54) COMPETITION BINDING ASSAY FOR DETECTING P2Y$_{ADP}$ RECEPTOR LIGANDS

(75) Inventor: Ian P. Kirk, Leics (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/462,294

(22) PCT Filed: Dec. 1, 1999

(86) PCT No.: PCT/SE99/02252

§ 371 (c)(1),
(2), (4) Date: Jan. 6, 2000

(87) PCT Pub. No.: WO00/33080

PCT Pub. Date: Jun. 8, 2000

(30) Foreign Application Priority Data

Dec. 2, 1998 (SE) ................................................ 9804175

(51) Int. Cl.$^7$ ..................... G01N 33/534; G01N 33/554; C07D 403/02
(52) U.S. Cl. ...................... 436/504; 435/7.1; 436/501; 436/804; 436/815; 544/254
(58) Field of Search ................................. 436/501, 504, 436/804, 815; 544/254; 435/7.1

(56) References Cited

U.S. PATENT DOCUMENTS

| 5,441,883 A | * | 8/1995 | Civelli et al. |
| 5,620,676 A | | 4/1997 | Jacobson et al. |
| 5,942,416 A | * | 8/1999 | Bergsma et al. |
| 5,981,223 A | * | 11/1999 | Sathe et al. |

FOREIGN PATENT DOCUMENTS

| WO | WO 96/29345 | * | 9/1996 |
| WO | 97/19170 | | 5/1997 |

OTHER PUBLICATIONS

Jin et al, "Molecular Basis for ADP–induced Platelet Activation," The Journal of Biological Chemistry, vol. 273, No. 4, pp. 2030–2034 (1998).
Hechler et al, "The P2Y$_1$ Receptor Is Necessary for Adenosine . . . ," Blood, vol. 92, No. 1, pp. 152–159 (1998).
Kunapuli et al, "P$_2$ receptor subtypes in the cardiovascular system," Biochem. J., vol. 336, pp. 513–523 (1998).

* cited by examiner

Primary Examiner—Mary E. Ceperley
(74) Attorney, Agent, or Firm—Nixon & Vanderhye

(57) ABSTRACT

The invention provides a competition binding assay for detecting P2Y$_{ADP}$ receptor ligands.

8 Claims, No Drawings

COMPETITION BINDING ASSAY FOR DETECTING P2Y$_{ADP}$ RECEPTOR LIGANDS

It is known that ADP (adenosine-5'-diphosphate) plays a pivotal role in terms of platelet function by causing adhesion, degranulation, shape change and aggregation of platelets via interaction with cell surface P2 receptors. It is the P2Y$_{ADP}$ receptor (formerly known as P$_{2T}$) that is primarily involved in mediating platelet aggregation, which is an as yet uncloned G-protein linked receptor. The pharmacological characteristics of this receptor have been described, for example, in the references by Humphries et al., Br. J. Pharmacology, (1994), 113, 1057–1063, and Fagura et al., Br. J. Pharmacology, (1998), 124, 157–164.

Compounds having antagonist activity at the P2Y$_{ADP}$ receptor are known, for example, from WO 98/28300, WO 97/03084, WO 94/18216 and EP-A-508 687 and are useful as anti-thrombotic agents in the treatment or prophylaxis of diseases such as unstable angina, coronary angioplasty (PTCA) and myocardial infarction.

It would be desirable to identify further compounds with binding activity at the P2Y$_{ADP}$ receptor, and also to identify further tissues/cell lines containing this receptor.

In accordance with the present invention, there is therefore provided a competition binding assay which comprises contacting a P2Y$_{ADP}$ receptor, preferably a human P2Y$_{ADP}$ receptor, with a P2Y$_{ADP}$ receptor radioligand and a candidate P2Y$_{ADP}$ receptor ligand, and measuring bound radioactivity.

The assay according to the present invention is very conveniently carried out on multi-well microtitre plates, thereby enabling a fast, simple and reproducible way of screening large numbers of potential P2Y$_{ADP}$ receptor ligands.

In the context of the present specification, the term "P2Y$_{ADP}$ receptor ligand", unless otherwise indicated, defines a ligand, e.g. an agonist or antagonist, of the P2Y$_{ADP}$ receptor other than a naturally-occurring ligand. The ligand may, for example, be a chemical compound, or a salt or solvate thereof.

The radioligand used in the assay is a substance which binds to the P2Y$_{ADP}$ receptor and which may be synthesised containing one or more radioactive atoms. Examples of substances which when radiolabelled may be used as the radioligand include:

(a) Compounds of formula (I)

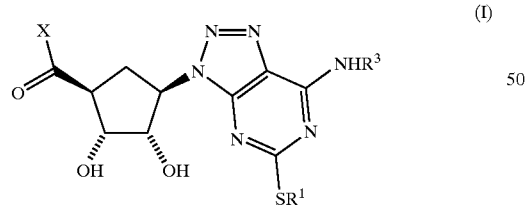

wherein
X is OH or NHR$^3$;
R$^1$ is C$_{1-6}$-alkyl, C$_{3-8}$-cycloalkyl or a phenyl group, each group being optionally substituted by one or more halogen atoms and/or OR$^4$, NR$^4$R$^5$, C$_{1-6}$-thioalkyl and/or C$_{1-6}$-alkyl (itself optionally substituted by one or more halogen atoms); R$^2$ is C$_{1-8}$-alkyl or C$_{2-8}$-alkenyl each of which is optionally substituted by one or more halogen atoms and/or OR$^4$, NR$^4$R$^5$, C$_{1-6}$-thioalkyl, C$_{3-8}$-cycloalkyl, aryl and/or C$_{1-6}$-alkyl groups; or R$^2$ is a C$_{3-8}$-cycloalkyl group optionally substituted by one or more halogen atoms and/or OR$^4$, NR$^4$R$^5$, C$_{1-6}$-thioalkyl, phenyl and/or C$_{1-6}$-alkyl groups; the optional phenyl substituent being further optionally substituted by one or more halogen atoms and/or NO$_2$, C(O)R$^4$, OR$^4$, NR$^4$R$^5$, C$_{1-6}$-thioalkyl and/or C$_{1-6}$-alkyl groups;

R$^3$ is hydrogen or C$_{1-6}$-alkyl substituted by one or more hydroxy and/or phenyl groups and optionally by one or more halogen atoms, wherein the phenyl group is substituted by one or more hydroxy groups and optionally substituted by one or more halogen atoms and/or NO$_2$, C(O)R$^4$, OR$^4$, NR$^4$R$^5$, C$_{1-6}$-thioalkyl and/or C$_{1-6}$-alkyl groups, or R$^3$ is a C$_{1-6}$-alkyl group substituted by a C(O)NR$^4$R$^5$ or a COOH group and optionally by one or more halogen atoms and/or OR$^4$, C(NH)NR$^4$R$^5$, C(O)NR$^4$R$^5$, phenyl and/or C$_{1-6}$-alkyl groups, wherein the alkyl group is optionally substituted by one or more hydroxy and/or phenyl groups and wherein the phenyl group is optionally substituted as defined above for R$^3$; or R$^3$ is a lactam ring of formula (i):

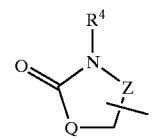

wherein Q is a (CH$_2$)$_m$ moiety wherein m is 1, 2 or 3, Z is O, C(O) or CH$_2$;
R$^4$ and R$^5$ each independently represent hydrogen, phenyl or a C$_{1-6}$-alkyl wherein the alkyl group is optionally substituted by one or more phenyl groups; and salts and solvates thereof;

(b) Compounds of formula (II)

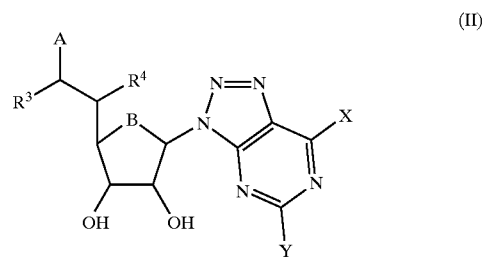

wherein
B is O or CH$_2$;
X is selected from NR$^1$R$^2$, SR$^1$ and C$_1$–C$_7$ alkyl;
Y is selected from NR$^1$R$^2$, SR$^1$ and C$_1$–C$_7$ alkyl;
R$^1$ and R$^2$ is each and independently selected from H, or C$_1$–C$_7$ alkyl optionally substituted upon or within the alkyl chain by one or more of O, S, N or halogen;
R$^3$ and R$^4$ are both hydrogen, or R$^3$ and R$^4$ together form a bond;
A is COOH, C(O)NH(CH$_2$)$_p$COOH, C(O)N[(CH$_2$)$_q$COOH]$_2$, C(O)NHCH(COOH)(CH$_2$)$_r$COOH or 5-tetrazolyl, wherein p, q and r is each and independently 1, 2 or 3; and salts and solvates thereof;

(c) Compounds of formula (I)

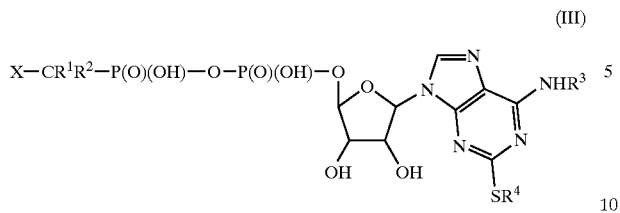

(III)

X—CR¹R²—P(O)(OH)—O—P(O)(OH)—O wherein $R^1$ and $R^2$ independently represent hydrogen or halogen;

$R^3$ and $R^4$ independently represent phenyl, or $C_1$–$C_6$ alkyl optionally substituted by one or more substituents selected from $OR^5$, $C_1$–$C_6$ alkylthio, $NR^6R^7$, phenyl, $COOR^8$ and halogen;

$R^5$, $R^6$, $R^7$ and $R^8$ independently represent hydrogen or $C_1$–$C_6$ alkyl;

X represents an acidic moiety; and salts and solvates thereof;

(d) Compounds of formula (IV)

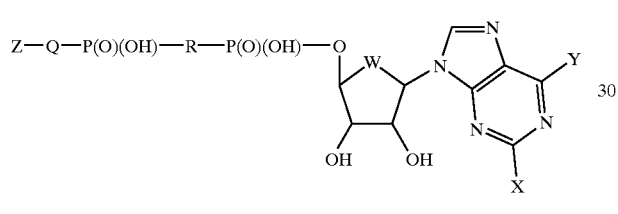

(IV)

Z—Q—P(O)(OH)—R—P(O)(OH)—O wherein

Q represents $CR^1R^2$;

R represents O or $CR^3R^4$;

W represents O or $CH_2$;

$R^1$, $R^2$, $R^3$ and $R^4$ independently represent hydrogen or halogen;

X represents $S(O)_nR^5$, $C_1$–$C_6$ alkyl, $C_1$–$C_6$ alkoxy, $C_1$–$C_6$ acylamino, $CONR^6R^7$, $NR^8R^9$, halogen, a 5- or 6-membered S containing heterocycle, or phenyl optionally substituted by $C_1$–$C_6$ alkyl;

n represents 0, 1 or 2;

$R^5$ represents aryl or $C_1$–$C_6$ alkyl optionally substituted by one or more substituents selected from hydroxy, $C_1$–$C_6$ alkoxy, halogen and aryl;

$R^6$, $R^7$, $R^8$ and $R^9$ independently represent hydrogen or $C_1$–$C_6$ alkyl;

Y represents $NH_2$ or $C_1$–$C_6$ alkoxy;

Z represents an acidic moiety;

in addition, when R represents $CR^3R^4$, then —Q—Z may also represent hydroxy or —OP(O)(OH)$_2$, provided that:
  i) when R is O, W is O, X is Cl, Y is $NH_2$ and Z is —P(O)(OH)$_2$, then $CR^1R^2$ does not represent $CH_2$; and
  ii) when R is O, W is O, X is $SCH_3$, Y is $NH_2$ and Z is —P(O)(OH)$_2$, then —$CR^1R^2$ does not represent $CH_2$, $CF_2$ or $CCl_2$; and salts and solvates thereof;

(e) Compounds of formula (V)

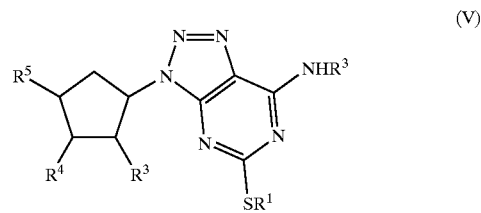

(V)

wherein $R^1$ is a $C_{1-6}$ alkyl, $C_{3-8}$-cycloalkyl or a phenyl group, each group being optionally substituted by one or more substituents selected from halogen, $OR^8$, $NR^9R^{10}$, $SR^{11}$ or $C_{1-6}$ alkyl (itself optionally substituted by one or more halogen atoms);

$R^2$ is $C_{1-8}$ alkyl optionally substituted by one or more substituents selected from halogen, $OR^8$, $NR^9R^{10}$, $SR^{11}$, $C_{3-8}$-cycloalkyl, aryl (optionally substituted by one or more alkyl groups and/or halogen atoms), or $C_{1-6}$-alkyl; or $R^2$ is a $C_{3-8}$-cycloalkyl group optionally substituted by one or more substituents selected from halogen, $OR^8$, $NR^9R^{10}$, $SR^{11}$, $C_{1-6}$-alkyl or phenyl (the latter two being optionally substituted by one or more substituents selected from halogen, $NO_2$, $C(O)R^8$, $OR^8$, $SR^{11}$, $NR^{12}R^{13}$, phenyl and $C_{1-6}$-alkyl which is optionally substituted by one or more halogen atoms);

one of $R^3$ or $R^4$ is hydroxy and the other is hydrogen, hydroxy or $NR^9R^{10}$;

$R^5$ is $(CH_2)_nNR^{14}R^{15}$ where n is 0 to 6 and $R^{14}$ and $R^{15}$ are independently hydrogen, $C_{1-6}$-alkyl or phenyl; or $R^5$ is $CONR^{16}R^{17}$ where $R^{16}$ is hydrogen or $C_{1-6}$-alkyl, and $R^{17}$ is $C_{1-6}$-alkyl or $C_{3-6}$-cycloalkyl each of which is substituted by $NR^{18}R^{19}$ and optionally substituted by phenyl, or $R^{17}$ is $C_{1-6}$-alkyl or $C_{3-6}$-cycloalkyl substituted by phenyl which is substituted by $NR^{18}R^{19}$ where $R^{18}$ and $R^{19}$ are independently hydrogen, $C_{1-6}$-alkyl or phenyl; or $R^{17}$ is a 5- to 8-membered saturated heterocycle containing one or more nitrogen atoms and optionally substituted on nitrogen by hydrogen, $C_{1-6}$-alkyl or phenyl;

or $R^{16}$ and $R^{17}$ together with the nitrogen atom to which they are attached form a 5- to 8-membered ring which is substituted by $NR^{18}R^{19}$ as defined above; or $R^{16}$ together with $R^{19}$ forms a 6- to 8-membered ring containing the two nitrogen atoms in which $R^{17}$ and $R^{18}$ are as defined above; or $R^5$ is $(CH_2)_pNR^{20}CO(CH_2)_qOR^{21}$ or $(CH_2)_pNR^{22}(CH_2)_qNR^{23}COR^{24}$ where p and q are independently 1 to 4 and $R^{20}$, $R^{21}$, $R^{22}$ $R^{23}$ and $R^{24}$ are independently $C_{1-4}$-alkyl or phenyl; or $R^5$ is $CH=CHCH_2NR^{25}R^{26}$ where $R^{25}$ is hydrogen, $C_{1-6}$ alkyl or phenyl and $R^{26}$ is hydrogen or $(CH_2)_yNR^{27}R^{28}$ where y is 2–4 and $R^{27}$ and $R^{28}$ are independently hydrogen, $C_{1-6}$ alkyl or phenyl;

$R^8$, $R^9$, $R^{10}$ and $R^{11}$ are independently hydrogen or $C_{1-6}$-alkyl; and $R^{12}$ and $R^{13}$ are independently hydrogen, $C_{1-6}$-alkyl or acyl groups;

and salts and solvates thereof;

(f) Compounds of formula (VI)

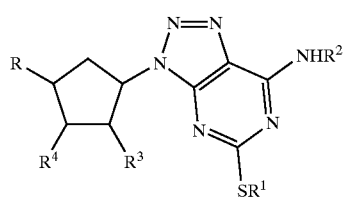

(VI)

wherein $R^1$ is a $C_{1-6}$ alkyl, $C_{2-6}$ alkenyl, $C_{2-6}$ alkynyl, $C_{3-8}$-cycloalkyl or a phenyl group, each group being optionally substituted by one or more substituents selected from halogen, $OR^8$ $NR^9R^{10}$, $SR^{11}$ or $C_{1-6}$ alkyl (itself optionally substituted by one or more halogen atoms);

$R^2$ is $C_{1-8}$ alkyl optionally substituted by one or more substituents selected from halogen $OR^8$, $NR^9R^{10}$, $SR^{11}$, $C_{3-8}$-cycloalkyl, aryl (optionally substituted by one or more alkyl groups and/or halogen atoms), or $C_{1-6}$-alkyl; or $R^2$ is a $C_{3-8}$-cycloalkyl group optionally substituted by one or more substituents selected from halogen, $OR^8$, $NR^9R^{10}$, $SR^{11}$, $C_{1-6}$-alkyl or phenyl, the latter two groups being optionally substituted by one or more substituents selected from halogen, $NO_2$, $C(O)R^8$, $OR^8$, $SR^{11}$, $NR^{12}R^{13}$, a fused 5- or 6-membered saturated ring containing one or two oxygen atoms, phenyl or $C_{1-6}$-alkyl the latter two groups being optionally substituted by $OR^8$, $NR^9R^{10}$ or one or more halogen atoms;

one of $R^3$ and $R^4$ is hydroxy and the other is hydrogen, hydroxy or $NR^9R^{10}$;

R is a group $(CR^5R^6)_mOR^7$ where m is 0 or 1, $R^5$ and $R^6$ are independently hydrogen, $C_{1-6}$ alkyl or phenyl the latter two groups being optionally substituted by halogen, and $R^7$ is hydrogen, $C_{1-6}$ alkyl or $(CR^5R^6)R^{14}$ where $R^5$ and $R^6$ are as defined above, n is 1 to 3 and, $R^{14}$ is COOH, $OR^{15}$, $NR^{15}R^{17}$ or $CONR^{16}R^{17}$;

or R is a $C_{1-4}$ alkyl or $C_{2-4}$ alkenyl group, each of which is substituted by one or more groups selected from =S, =O, =$NR^{20}$ or $OR^{21}$ and optionally substituted by one or more groups selected from halogen, $C_{1-4}$ alkyl, phenyl, $SR^{21}$, $NO_2$ or $NR^{22}R^{23}$ (where $R^{21}$, $R^{22}$, and $R^{23}$ are independently hydrogen, $C_{1-4}$ alkyl or phenyl; $R^{20}$ is $OR^{24}$ or $NR^{25}R^{26}$, where $R^{24}$ is hydrogen, $C_{1-4}$ alkyl or phenyl, and $R^{25}$ and $R^{26}$ are independently hydrogen, $C_{1-4}$ alkyl, aryl, $C_{1-6}$ acyl, arylsulphonyl or arylcarbonyl);

$R^8$ is hydrogen, $C_{1-6}$ alkyl optionally substituted by halogen or $R^8$ is phenyl optionally substituted by one or more substituents selected from halogen, $NO_2$, $C(O)R^6$, $OR^6$, $SR^9$, $NR^{10}OR^{11}$;

$R^9$, $R^{10}$ and $R^{11}$ are independently hydrogen or $C_{1-6}$ alkyl;

$R^{12}$ and $R^{13}$ are independently hydrogen, $C_{1-6}$ alkyl, acyl, alkyl sulfonyl optionally substituted by halogen, or phenyl sulfonyl optionally substituted by $C_1$–$C_4$ alkyl; and $R^{15}$, $R^{16}$ and $R^{17}$ are independently hydrogen or $C_{1-6}$ alkyl; and salts and solvates thereof; and (g) Compounds of formula (VII)

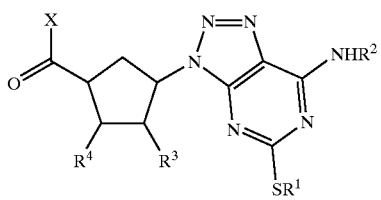

(VII)

wherein $R^1$ is a $C_{1-6}$ alkyl, $C_{3-8}$-cycloalkyl or a phenyl group, each group being optionally substituted by one or more substituents selected from halogen, $OR^6$, $NR^7R^8$, $SR^9$ or $C_{1-6}$ alkyl (itself optionally substituted by one or more halogen atoms);

$R^2$ is $C_{1-8}$ alkyl optionally substituted by one or more substituents selected from halogen, $OR^6$, $NR^7R^8$, $SR^9$, $C_{3-8}$-cycloalkyl, aryl (optionally substituted by one or more alkyl groups and/or halogen atoms), or $C_{1-6}$-alkyl; or $R^2$ is a $C_{3-8}$-cycloalkyl group optionally substituted by one or more substituents selected from halogen, $OR^6$, $NR^7R^8$, $SR^9$, $C_{1-6}$-alkyl or phenyl (the latter two being optionally substituted by one or more substituents selected from halogen, $NO_2$, $C(O)R^6$, $OR^6$, $SR^9$, $NR^{10}R^{11}$, phenyl and $C_{1-6}$-alkyl which is optionally substituted by one or more halogen atoms);

one of $R^3$ or $R^4$ is hydrogen and the other is hydroxy;

X is OH or $NHR^5$;

R is a $C_{1-6}$-alkyl group substituted by COOH or C(O)$NR^7R^8$ and optionally by one or more further substituents selected from halogen, $OR^{12}$, $C(NH)NR^{13}R^{14}$, $C(O)NR^{15}R^{16}$, phenyl (optionally substituted by one or more groups selected from halogen, $NO_2$, $C(O)R^6$, $OR^{20}$, $NR^7R^8$, $SR^9$ and $C_{1-6}$-alkyl) or $C_{1-6}$-alkyl (optionally substituted by one or more hydroxy or phenyl groups);

or $R^5$ is a lactam ring of formula (i):

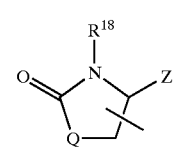

(i)

wherein Q is a $(CH_2)_m$ moiety where m is 1, 2 or 3, Z is O, C(O) or $CH_2$ and $R^{18}$ is hydrogen or $C_{1-6}$-alkyl; $R^6$, $R^9$, $R^{12}$, $R^{13}$, $R^{14}$, $R^{15}$ and $R^{16}$ are independently hydrogen or $C_{1-6}$-alkyl;

$R^7$ and $R^8$ are independently hydrogen, $C_{1-6}$-alkyl (optionally substituted by one or more phenyl groups) or phenyl groups; and $R^{10}$ and $R^{11}$ are independently hydrogen, $C_{1-6}$-alkyl or acyl groups;

and salts and solvates thereof.

Compounds of formulae (I), (II), (III), (IV), (V), (VI) and (VII) are disclosed respectively in WO 98128300, WO 97/03084, WO 94/18216, EP-A-508 687, PCT/SE98/01392, PCT/SE98/01393 and PCT/SE98/01394 and the contents of these seven documents are incorporated herein by reference.

Examples of suitable salts that may be used include alkali metal (e.g. sodium or potassium), alkaline earth metal (e.g. calcium or magnesium), Group III metal (e.g. aluminium), ammonium, hydrochloride, hydrobromide, phosphate, acetate, fumarate, maleate, tartrate, citrate, oxalate, methanesulphonate and p-toluenesulphonate salts.

The techniques for radiolabelling substances may be those conventionally used in the art and therefore the radioligand may be prepared by methods known in the art.

The radioligand is most preferably a radiolabelled compound of formula (I) or(II) or a salt or solvate thereof, and is especially $[^{125}I]$-[1S-[1α,2β,3β,4α(E)]]-2,3-dihydroxy-4-[7-3-iodo-prop-2-enylamino)-5-(propylthio)-3H-1,2,3-triazolo[4,5-d]pyrimidin-3-yl]-cyclopentanecarboxylic acid, or $[^{3}H]$-[1S-(1α,2β,3β,4α)]-4-[7-(butylamino)-5-(propylthio)-3H-1,2,3-triazolo-[4,5-d]pyrimidin-3-yl]-2,3-dihydroxy-cyclopentanepropanoic acid, or a salt or solvate of any one thereof.

Advantageously, the radioligand has a specific activity of greater than 10 Ci/mmol and a $P2Y_{ADP}$ receptor activity ($IC_{50}$) of less than 1 micromolar ($\mu M$).

In the context of the present specification, "specific activity" is defined as the activity per unit mass of substance containing a radioactive nuclide and is normally expressed as millicuries per milligram (mCi/mg) (kBq/mg), as millicuries per millimole (mCi/mmol) (kBq/mmol), or as curies per millimole (Ci/mmol) (GBq/mmol); and "$P2Y_{ADP}$ receptor activity ($IC_{50}$)" is defined as the concentration, expressed in micromolar units, of radioligand required to inhibit the maximal aggregation response elicited by ADP according to the platelet aggregation assay as described in WO 98/28300. The platelet aggregation assay, which uses washed human platelets, is carried out in the following manner.

Human venous blood (100 ml) is divided equally between 3 tubes, each containing 3.2% trisodium citrate (4 ml) as anticoagulant. The tubes are centrifuged for 15 minutes at 240 G to obtain a platelet-rich plasma (PRP) to which 300 ng/ml prostacyclin is added to stabilize the platelets during the washing procedure. Red cell free PRP is obtained by centrifugation for 10 minutes at 125 G followed by further centrifugation for 15 minutes at 640 G. The supernatant is discarded and the platelet pellet resuspended in modified, Calcium Free Tyrode solution (10 ml) (CFT), composition: NaCl 137 mM, $NaHCO_3$ 11.9 mM, $NaH_2PO_4$ 0.4 mM, KCl 2.7 mM, $MgCl_2$ 1.1 mM, dextrose 5.6 mM, gassed with 95% $O_2$/5% $CO_2$ and maintained at 37° C. Following addition of a further 300 ng/ml $PGI_2$, the pooled. suspension is centrifuged once more for 15 minutes at 640 G. The supernatant is discarded and the platelets are resuspended initially in 10 ml CFT with further CFT added to adjust the final platelet count to $2\times10^5$/ml. This final suspension is stored in a 60 ml syringe at 3° C. with air excluded. To allow recovery from $PGI_2$-inhibition of normal function, platelets are used in aggregation studies no sooner than 2 hours after final resuspension.

Aliquots of platelet suspension (3 ml) are added to tubes containing $CaCl_2$ solution (60 $\mu l$ of 50 mM solution with a final concentration of 1 mM). Human fibrinogen (Sigma, F 4883) and 8-sulphophenyltheophylline (8-SPT, which is used to block any $P_1$-agonist activity of test substance) are added to give final concentrations of 0.2 mg/ml (60 $\mu l$ of 10 mg/ml solution of clottable protein in saline) and 300 nM (10 $\mu l$ of 15 mM solution in 6% glucose), respectively. Platelets or buffer as appropriate are added in a volume of 150 $\mu l$ to the individual wells of a 96 well plate. All measurements are made in triplicate in platelets from each donor.

Aggregation responses in 96 well plates are measured using the change in absorbance given by the plate reader at 660 nm. Either a Bio-Tec Ceres 900C or a Dynatech MRX are used as the plate reader.

The absorbance of each well in the plate is read at 660 nm to establish a baseline figure. Saline or the appropriate solution of test substance (e.g. the radioligand) is added to each well in a volume of 10 gl to give a final concentration of 0, 0.01, 0.1, 1, 10 or 100 mM. The plate is then shaken for 5 minutes on an orbital shaker on setting 10 and the absorbance read at 660 nm. Aggregation at this point is indicative of agonist activity of the test substance. Saline or ADP (30 mM; 10 $\mu l$ of 450 mM) is then added to each well and the plate shaken for a further 5 minutes before reading the absorbance again at 660 nm. The concentration of test substance that produces a response which is half the maximum control ADP response is the $IC_{50}$ value.

According to a preferred embodiment of the invention, the competition binding assay comprises (i) isolating and washing human platelets or human platelet membranes, (ii) incubating the platelets or platelet membranes with a $P2Y_{ADP}$ receptor radioligand and a candidate $P2Y_{ADP}$ receptor ligand, (iii) filtering and washing the platelets or platelet membranes, and (iv) measuring bound radioactivity.

In step (i) above, methods for isolating and washing human platelets or human platelet membranes are known in the art, e.g. as described by Connolly et al. (1992), J. Biol. Chem., 267, 6893–6898 and Biochim. et Biophys. Act. (1986), 854, 67–76.

In step (ii), the incubation is conveniently carried at a temperature in the range from 4 to 37° C., for a period of time of from 5 to 120 minutes.

The present invention further provides the use of $[^{125}I]$-[1S-[1α,2β,3β,4α(E)]]-2,3-dihydroxy-4-[7-(3-iodo-prop-2-enylarnino)-5-(propylthio)-3H-1,2,3-triazolo[4,5-d]pyrimidin-3-yl]-cyclopentanecarboxylic acid, or $[^{3}H]$-[1S-(1α,2β,3β,4α)]-4-[7-(butylamino)-5-(propylthio)-3H-1,2,3-triazolo-[4,5-d]pyrimidin-3-yl]-2,3-dihydroxy-cyclopentanepropanoic acid, or a salt or solvate of any one thereof, as a $P2Y_{ADP}$ receptor radioligand in a competition binding assay as hereinbefore defined.

The present invention will now be further illustrated by reference to the following Examples.

EXAMPLE 1

Synthesis of $[^{3}H]$-[1S-(1α,2β,3β,4α]-4-[7-(Butylamino)-5-(propylthio)-3H-1,2,3-triazolo-[4,5-d]pyrinidin-3-yl]-2,3-dihydroxy-cyclopentanepropanoic Acid, Sodium Salt A flask containing [1R-[1α(E),2β,3β,4α]]-3-[4-[7-(butylamino)-5-(propylthio)-3H-1,2,3-triazolo[4,5-d]pyrimidin-3-yl]-2,3-dihydroxycyclopentyl]-2-propenoic acid (5.5 mg) (prepared as described in Example 3 of WO 97/03084) in ethanol (1 ml), containing palladium on carbon (5% w/w Pd, 1 mg) was attached to a tritium manifold, evacuated and tritium gas (10 Ci, 57.6 Ci mmol$^{-1}$, 174 $\mu mol$) introduced. The reaction was stirred for 18 hours at room temperature, then the catalyst removed by filtration and the remaining tritium removed by lyophilisation with ethanol (2×1 ml). Purification (HPLC, Symmetry C8, 45% acetonitrile/0.025% v/v aqueous acetic acid as eluant) gave the title acid which was converted to the sodium salt. The salt was dissolved in ethanol (16ml) to afford a solution of the title compound (1 mCi ml$^{-1}$, 24 Ci mmol$^{-1}$). The product was characterised by comparison with unlabelled compound (prepared as described in Example 3 of WO 97/03084)

(HPLC, Symmetry C8, 50% methanol/0.1% w/v aqueous ammonium acetate to 95% methanol over 10 minutes as eluant).

EXAMPLE 2

Synthesis of [$^{125}$I]-[1S-[1 α,2β,3β,4α(E)]]-2,3-Dihydroxy-4-[7-(3-iodo-prop-2-enylamino)-5-(propylthio)-3H-1,2,3-triazolo[4,5-d]pyrimidin-3-yl]-cyclopentanecarboxylic Acid

[3aR-[3aα,4α,6α(E),6aα]]-6-[7-(3-Tributylstannyl-prop-2-enylamino)-5-(propylthio)-3H-1,2,3-triazolo[4,5-d]pyrimidin-3-yl]-tetrahydro-2,2-dimethyl-4H-cyclopenta-1,3-dioxole-4-carboxylic acid (1.66 nmol) (prepared as described in Example 93 of WO 98/28300) in acetonitrile (40 μl) was added to sodium [$^{125}$I] Iiodide (obtained from Amersham International) (1 mCi, 10 μl, 0.5 nmol), followed by a solution of chloramine-T in water (7 μl, 1.5 nmol). The vial was sealed, shaken vigorously, then left to stand at room temperature for 1 hour. Aqueous trifluoroacetic acid (25% v/v, 50 μl) was then added and the reaction mixture resealed, shaken and left to stand for a further 2 hours. Purification (HPLC, Novapak C18, 30% acetonitrile/0.5% w/v aqueous ammonium actate then increased to 95% acetonitrile as eluant) gave the title compound, to which ethanol was added to the required volume. The product was characterised by comparison with unlabelled compound (prepared as described in Example 93 of WO 98/28300) (HPLC symmetry shield C8 75×3.9 mm, 25% acetonitrile/0.5% w/v aqueous ammonium acetate increased to 95% acetonitrile over 3 minutes and held for 3 minutes, 2 ml min$^{-1}$, retention time=2.98 minutes).

EXAMPLE 3

Washed Platelet Prearation

Human venous blood (100 ml), obtained from healthy volunteers was divided equally between 3 tubes, each containing 3.2% trisodium citrate (4 ml) as an anti-coagulant. The tubes were centrifuged for 15 min at 240 G to obtain platelet-rich plasma (PRP) to which prostacyclin (PGI$_2$ 300 ng·ml$^{-1}$) was added to stabilize platelets during the washing procedure. Red cell-free PRP was obtained by centrifugation for 10 minutes at 125 G and following further centrifugation for 15 minutes at 640 G, the supernatant was discarded and the platelet pellet in each tube resuspended in modified, calcium-free, Tyrodes solution (10 ml) (CFT, composition: NaCl, 137.0 mM; NaHCO$_3$, 11.9 mM; NaH$_2$PO$_4$, 0.4 mM; KCl, 2.7 mM; MgCl$_2$, 1.1 mM and dextrose, 5.55 mM), gassed with 95% O$_2$/5% CO$_2$ and maintained at 37° C. Following addition of PGI$_2$ (300 ng·ml$^{-1}$), the pooled suspension was centrifuged once more for 15 minutes at 640 G. The supernatant was discarded and the platelets resuspended in CFT to give a final platelet count of 200–250×10$^3$.μl$^{-1}$. The platelets were used within 30 min for radioligand binding studies.

EXAMPLE 4

Binding Assays

Binding assays were performed in 96-well plates, with each well containing 250 μl aliquots of CFT consisting of 50 μl 0.1 μCi[$^{125}$I]-[1S-[(1α,2β,3β,4α(E)]]-2,3-dihydroxy4-[7-(3-iodo-prop-2-enylamino)-5-(propylthio)-3H-1,2,3-triazolo[4,5-d]pyrimidin-3-yl]-cyclopentanecarboxylic acid (final concentration 0.18 nM) or 50 μl 0.1 μCi[$^3$H][1S-(1α, 2β,3β,4α)]-4-[7-(Butylamino)-5-(propylthio)-3H-1,2,3-triazolo-[4,5-d]pyrimidin-3-yl]-2,3-dihydroxy-cyclopentanepropanoic acid, sodium salt (final concentration 17 nM) and 200 μl of washed platelets at a concentration of 200–250×10$^3$.μl$^{-1}$ (final concentration 160–200×10$^3$.μl$^{-1}$). All putative P2Y$_{ADP}$ ligands were tested in duplicate over the appropriate concentration range by addition of 5 μl of compound prior to adding the radioligand, with appropriate solvent controls being performed in parallel. The plates were incubated for 30 min at room temperature on a plate shaker (Stuart scientific; model S01, setting 6) prior to terminating the reactions by filtration. Filtration was performed using a MACHIII cell harvester with 2×2s wash periods (with CFT) on to Whatman GF/B filter plates for platelets incubated [$^{125}$I][1S-[1α,2β,3β,4α(E)]]-2,3-dihydroxy-4-[7-(3-iodo-prop-2-enylamino)-5-(propylthio)-3H-1,2,3-triazolo[4,5-d]pyrimidin-3-yl]-cyclopentanecarboxylic acid or a Wallac cell harvester using glass fibre printed filtermats type A, with a 7s wash time (with CFT) for platelets incubated with [$^3$H]-[1S-(1α,2β,3β,4α) ]-4-[7-(Butylamino)-5-(propylthio)-3H-1,2,3-triazolo [4,5-d]pyrimidin-3-yl]-2,3-dihydroxy-cyclopentanepropanoic acid, sodium salt. The resultant filterplates were then, in the case of the MACHI, sealed and Microscint 20 (50 gl) added prior to determination of [$^{125}$I] levels by scintillation counting on a Packard Topcounter or, in the case of the Wallac filtermats, the individual wells were punched into vials containing 5 ml scintillation fluid for determination of [$^3$H] levels in a beta counter.

Non-specific binding was determined in the presence of the standard P2Y$_{ADP}$ antagonist, 2-propylthio-D-β,γ-dichloromethylene ATP (10 μM), as described by Humphries et al., Br. J. Pharmacology (1995), 115, 1110–1116.

Results were expressed as specific binding in CPM/DPM and were calculated by subtracting the non-specific binding from the total binding achieved at each concentration. For each test compound, a binding affinity (IC$_{50}$) was calculated by linear interpolation of the concentration/inhibition curve, using the software package Excel. The IC$_{50}$ value being the concentration at which a 50% reduction in specific binding of either [$^{125}$I[-]1S-[1α,2β,3β,4α(E)]]-2,3-dihydroxy-4-[7-(3-iodo-prop-2-enylamino)-5-(propylthio)-3H-1,2,3-triazolo[4,5-d]pyrimidin-3-yl]-cyclopentanecarboxylic acid or [$^3$H]-[1S-(1α,2β,3β,4α)]-4-[7-(butylamino)-5-(propylthio)-3H-1,2,3-triazolo-[4,5-d]pyrirnidin-3-yl]-2,3-dihydroxy-cyclopentanepropanoic acid, sodium salt was achieved. Results were reported as pKi values which are equal to the negative, logarithm of the IC$_{50}$ (pIC$_{50}$) in this system (Cheng Prusoff). In cases where there was insufficient displacement of binding to calculate a pKi value, the activities were reported as being <6.

What is claimed is:

1. A competition binding assay to identify a P2Y$_{ADP}$ receptor ligand, which comprises contacting a P2Y$_{ADP}$ receptor with a P2Y$_{ADP}$ receptor radioligand and a candidate P2Y$_{ADP}$ receptor ligand, and measuring reactivity bound to the P2Y$_{ADP}$ receptor, wherein the radioligand is selected from the group consisting of [$^{125}$I]-1S-[1a, 2b,3b,4a(E)]]-2,3-dihydroxy-4-[7-(3-iodo-prop-2-enylamino)-5-(propylthio)-3H-1,2,3-triazolo[4,5-d]pyrimidin-3-yl]-cyclopentanecarboxylic acid, [$^3$H]-[1S-(1α,2β,3β,4α)]-4-[7 (butylamino)-5-(propylthio)-3H-1,2,3-triazolo-[4,5-d] pyrimidin-3-yl]-2,3-dihydroxy-cyclopentanepropanoic acid, salts and solvates thereof.

2. An assay according to claim 1, wherein the P2Y$_{ADP}$ receptor is of human origin.

3. An assay according to claim 2 which comprises:
(i) isolating and washing human platelets or human platelet membranes,
(ii) incubating the platelets or platelet membranes with a P2Y$_{ADP}$ receptor radioligand and a candidate P2Y$_{ADP}$ receptor ligand,
(iii) filtering and washing the platelets or platelet membranes, and
(iv) measuring radioactivity bound to the platelets or platelet membranes.

4. An assay according to claim 1, wherein the radioligand has a specific activity greater than 10 Ci/mmol and a P2Y$_{ADP}$ receptor activity (IC$_{50}$) of less than 1 micromolar ($\mu$M).

5. [$^{125}$I]-1S-[1α, 2β,3β,4α(E)]]2,3-dihydroxy-4-[7-(3-iodo-prop-2-enylamino)-5-(propylthio)-3H-1,2,3-triazolo [4,5-d]pyrimidin3-yl]-cyclopentanecarboxylic acid, salts and solvates thereof.

6. [$^3$H]-[1S-(1α,2β, 3β,4α)]-4-[7-(butylamino)-5-(propylthio)-3H-1,2,3-triazolo-[4,5-d]pyrimidin-3-yl]-2,3-dihydroxy-cyclopentanepropanoic acid, salts and solvates thereof.

7. [$^{125}$I]-1S-[1α,2β,3β,4α(E)]]2,3-dihydroxy-4-[7-(3-iodo-prop-2-enylamino)-5-(propylthio)-3H-1,2,3-triazolo [4,5-d]pyrimidin-3-yl]-cyclopentanecarboxylic acid, salts and solvates thereof, having a specific activity greater than 10 Ci/mmol.

8. [$^3$H]-[1S-(1α,2β,3β,4α)]4-[7-(butylamino)-5-(propylthio)-3H-1,2,3-triazolo-[4,5-d]pyrimidin-3-yl]-2,3-dihydroxy-cyclopentanepropanoic acid, salts and solvates thereof, having a specific activity greater than 10 Ci/mmol.

* * * * *